US007983935B1

(12) United States Patent
Carricarte et al.

(10) Patent No.: US 7,983,935 B1
(45) Date of Patent: Jul. 19, 2011

(54) SYSTEM AND METHOD FOR AUTOMATICALLY AND ITERATIVELY PRODUCING AND UPDATING PATIENT SUMMARY ENCOUNTER REPORTS BASED ON RECOGNIZED PATTERNS OF OCCURRENCES

(75) Inventors: Andrew L. Carricarte, Miami, FL (US); Jose M. Sanchez, Miami Springs, FL (US)

(73) Assignee: IOS Health Systems, Inc., Miami, FL (US)

( * ) Notice: Subject to any disclaimer, the term of this patent is extended or adjusted under 35 U.S.C. 154(b) by 0 days.

(21) Appl. No.: 12/728,850

(22) Filed: Mar. 22, 2010

(51) Int. Cl.
*G06Q 50/00* (2006.01)
*G06Q 10/00* (2006.01)

(52) U.S. Cl. .............................................. 705/2; 705/3
(58) Field of Classification Search ................. 705/2
See application file for complete search history.

(56) References Cited

U.S. PATENT DOCUMENTS

| 4,872,122 | A | * | 10/1989 | Altschuler et al. ............ 356/432 |
| 5,583,758 | A | * | 12/1996 | McIlroy et al. ................... 705/2 |
| 6,988,088 | B1 | | 1/2006 | Miikkulainen |
| 7,315,825 | B2 | | 1/2008 | Rosenfeld |
| 7,379,885 | B1 | | 5/2008 | Zakim |
| 2003/0204415 | A1 | | 10/2003 | Knowlton |
| 2004/0078228 | A1 | | 4/2004 | Fitzgerald |
| 2004/0103001 | A1 | | 5/2004 | Mazar |
| 2005/0273363 | A1 | | 12/2005 | Lipscher |
| 2006/0036471 | A1 | | 2/2006 | Sanjay-Gopal |
| 2007/0203761 | A1 | | 8/2007 | Keen |

OTHER PUBLICATIONS

Chauhan, A computer-aided MFCC-based HMM system for automatic auscultation, Computers in Biology and Medicine, vol. 38, Issue 2, Feb. 2008, pp. 221-233.*

* cited by examiner

*Primary Examiner* — Luke Gilligan
*Assistant Examiner* — Tran Nguyen
(74) *Attorney, Agent, or Firm* — Novak Druce + Quigg LLP

(57) ABSTRACT

A method for automatically and iteratively updating patient encounter reports based on recognized patterns of occurrences. A patient's information is obtained prior to a visit to a healthcare facility. This information is compared to a set of guidelines. The result is a preliminary patient encounter report that may be presented to a physician as well as act as a preset trigger to generate financial transactions. The physician can edit the report due to his own preferences and the updated report automatically sent to a rules engine that examines the edits, on a physician, healthcare facility, and patient level and determines if changes to the existing guidelines need to be made. The new guidelines are sent to a predictor module so that upon subsequent visits by patients, new guidelines will appear on the preliminary patient encounter summary report along with other learned administrative and financial transactions within the system.

20 Claims, 15 Drawing Sheets

SYSTEM AND METHOD FOR AUTOMATICALLY AND ITERATIVELY PRODUCING AND UPDATING PATIENT SUMMARY ENCOUNTER REPORTS BASED ON RECOGNIZED PATTERNS OF OCCURRENCES

FIELD OF THE INVENTION

The present invention relates to a method and system for processing electronic medical records and more specifically to a method and system for utilizing a patient's existing financial, medical, and demographic information to automatically and iteratively create patient summary reports and financial transactions that are continually revised and updated due to the recognition of repeated occurrences at a physician, medical practice or patient level.

BACKGROUND OF THE INVENTION

The medical industry has been slow to react to the many technological improvements that have taken place in the field of electronic medical records processing. Many physicians are reluctant to move away from the archaic methods they are used to and were trained in for many years. These include a medical practice that relies heavily on the manual input of patient information, the maintenance of drawers full of patients' paper records, and the handwritten entries by the physician and his or her staff. While some medical practices have upgraded their infrastructure by using electronic medical records as opposed to paper records, many of these types of systems incorporate multiple sources and require numerous functions in order for the physician and his or her staff to adequately process a patient and update their records after a patient visit.

For example, if a patient shows up at a physician's office for the first time, the staff will first have to obtain the patient's information and demographics, including their insurance carrier, past medical history, history of family illnesses, current ailments, current medication, past surgeries, test results, referring physician, etc. Once this information is obtained, the staff must first contact one source—the patient's insurance company to verify eligibility, then contact another source—to obtain credit card information from the patient, and then create a patient file. The patient can then be seen by the doctor who may or may not have immediate access to the patient's medical history. The physician, in order to examine the patient, may refer to a variety of different outdated sources and libraries in order to properly diagnose the patient's ailment. After examining the patient, the physician must then document the visit in a format that covers his subjective review, objective evaluation, assessment and plan of care. In order to do this, the physician must review the patient's past history, perhaps use medical references for evaluation, prescribe medication, place orders for laboratory work, administer a referral, and then document the services he provided in order to code the appropriate level of care for reimbursement purposes. The patient then makes final payment, schedules a follow-up visit, and receives any paperwork necessary for follow up actions (prescriptions, lab work, etc.).

Most of the actions outlines above are typically performed on independent pieces of paper of on different parts of an electronic data system. The result is a severe lack of efficiency which can lead to degradation of care or finances due to incomplete or erroneous actions throughout the cumbersome and fragmented process. Further, existing systems do not recognize repeated patterns of occurrences due to a physician's input, common or repeated medical practice behavior, or commonality in patient data of financial transactions.

Therefore, what is needed is an electronic medical records system that retrieves and stores a patient's vital information, and creates a readable, updatable, and real-time patient summary report taking into account recognizable patterns of medical practice, physician and patient procedure, in order to increase patient visit efficiency and throughput.

SUMMARY OF THE INVENTION

The present invention advantageously provides a method, system, and computer program product for automatically and iteratively updating and automating patient summary encounter reports and financial transactions based on a recognized pattern of practice, physician, or patient occurrences. The inventive system, method and computer program product accomplishes this by obtaining a patient's medical, financial, and demographic information prior to a visit to a medical facility. Once this information is obtained, it is reviewed and once accepted, compared to a pre-defined set of guidelines and rules. The result is a preliminary patient encounter summary report that may be presented to a physician at the medical facility prior to the patient examination. The physician can edit the report due to his or her own preferences. Upon editing, the report is automatically updated and the edits are sent to a rules engine that examines the edits and determines if changes to the existing guidelines and rules need to be made. At the same time, a series of events can be initiated that relate to post-visit activities including the prescribing of medication, setting up lab tests, generating letters to other physicians and performing automatic financial transactions, copays, patient balances, and the like. If the rules engine determines that new rules are warranted due to a recognized pattern or due to occurrences that exceed a threshold amount, the new rules are sent to a predictor module so that upon subsequent visits by patients, the new rules and guidelines will appear on the preliminary patient encounter summary report presented to the physician.

In one aspect of the invention, a method for automatically and iteratively updating patient encounter reports is provided. The method includes applying patient information to stored rules to produce a preliminary patient encounter report, where the preliminary patient encounter report includes predicted activity for a patient encounter, presenting the preliminary patient encounter report for editing and if editing of the predicted activity occurs, producing an updated patient encounter report containing updated predicted activity, determining if the updated predicted activity forms a recognizable pattern, and if the updated predicted activity forms a recognizable pattern, generating a subsequent patient encounter summary report that replaces the predicted activity with the updated predicted activity.

In another aspect of the invention, a system for automatically and iteratively updating patient encounter reports is provided. The system includes a database for storing patient data, a predictor module for applying the patient data to a set of rules to produce a patient preliminary encounter report, the patient preliminary encounter report adapted to receive annotations by a user, the annotations resulting in updated predicted activity, and a rules engine having a processor for determining if the updated predicted activity forms a recognizable pattern, wherein if the updated predicted activity forms a recognizable pattern, the processor generates a subsequent patient encounter summary report that replaces the predicted activity with the updated predicted activity.

In yet another aspect, a computer program product tangibly embodied in a computer storage medium for executing instructions on a processor is provided. The computer program product being operable to cause a machine to apply patient information to a stored set of rules to produce a preliminary patient encounter report, the preliminary patient encounter report including predicted activity for a patient encounter, produce an updated patient encounter report containing updated predicted activity, determine if the updated predicted activity form a recognizable pattern, and, if the updated predicted activity form a recognizable pattern, generate a subsequent patient encounter summary report that replaces the predicted activity with the updated predicted activity.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 8 is a depiction of an exemplary computer screen showing the imported information entered for the patient in accordance with the principles of the present invention;

FIG. 9 is a depiction of an exemplary computer screen offering additional input selections for the patient in accordance with the principles of the present invention;

DETAILED DESCRIPTION OF THE INVENTION

The present invention is directed towards a system, method, and computer program product for automatically and iteratively updating patient encounter reports and financial transactions for patient visits to a medical provider by providing a predictor module and rules engine that takes into account recognized patient behavior patterns, a patient's clinical and financial history, existing medical guidelines, and operational rules such that the physician and his or her staff are presented with a real time medical profile for each patient. The system automatically retrieves a patient's history, including their current medical status and personal and financial information, and applies this information towards a shared or recognized database of existing rules. The result is a clinical "summary" profile for that patient, specific to the treatment or service applied. The physician, presented with this summary profile, can alter it by, for example, applying a different treatment to an illness. The system records these changes and, once a specific threshold is exceeded or a pattern recognized, new algorithms are invoked resulting in the display of these alterations in future summary profiles. Thus, the system of the present invention "learns" of changes to standard procedures at a number of different levels while continuously monitoring the entry, alteration, and access of clinical, operational and financial data in order to streamline the delivery of medical services to patients.

Figure 1:
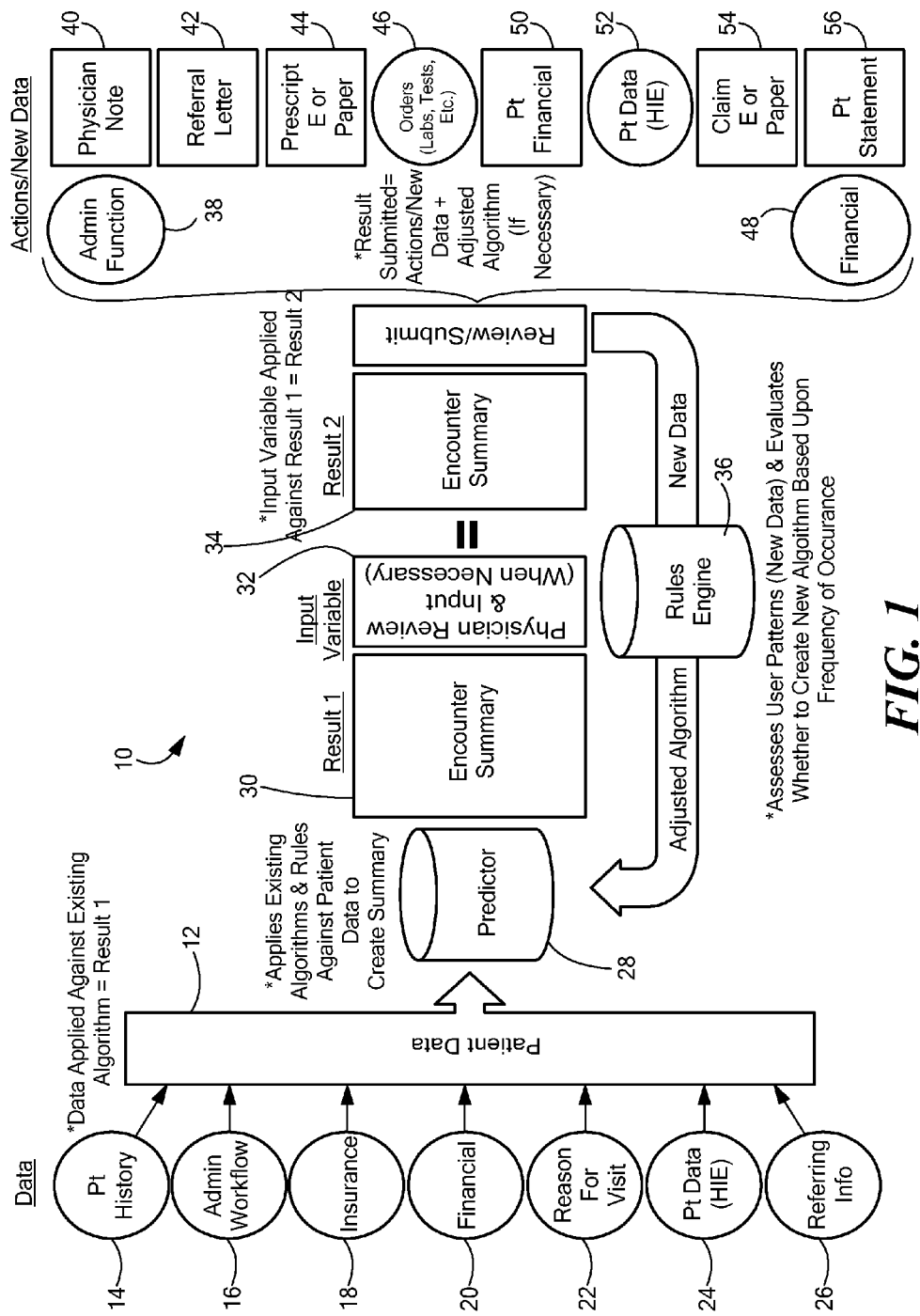
FIG. 1 is a block diagram of system constructed in accordance with the principles of the present invention.

Referring now to the drawing figures in which like reference designators refer to like elements, there is shown in FIG. 1 a diagram of an exemplary embodiment of system 10 of the present invention. For each patient visiting a medical facility, system 10 receives data 12 specific for that patient. The patient may provide the data themselves via a written form that they fill out, over the phone or via electronic means such as e-mail or by providing access to a web portal. Alternately, system 10 may retrieve the patient data 12 from one or more sources. For example, the patient data 12 may include a patient's previous medical history 14, which can be obtained from the patient's previous physician, or from an external source such as a shared health network, national database, or Health Information Exchange ("HIE") using standard healthcare transmissions such as Healthcare Information Technology Standards Panel (HITSP) or Health Level Seven ("HL7"). Thus, the invention is not limited in the method that patient data 12 is obtained by system 10.

In addition to receiving the patient's medical history, system 10 retrieves the patient's biographical, demographic information and other administrative and/or financial information 16 in order to initiate the patient into the workflow for that particular medical service provider. Other information such as insurance information 18 in order to verify the patient's eligibility with their insurance company, and the patient's payment and financial information 20, is also retrieved. Additional information such as the reason for the patient's visit 22, general patient data retrieved for example from the Health Information Exchange (HIE) 24, and information from a referring physician 26 may also be obtained. It should be noted that the different kinds of patient data 12 shown in FIG. 1 is meant to be illustrative only and the invention is not limited to only the patient information shown in the figure. Other types of information related to the patient can also be obtained. Thus, the types of patient data 12 obtained by system 10 may be only a portion of the types shown in FIG. 1, and also may include other types of data not shown. The patient information 12, once obtained, is stored in a database either within the medical facility where the patient is visiting, or remotely. The patient data 12 is retrievable and sortable using any commonly known database application software.

FIG. 1 also shows a predictor module 28, which includes a processor, hardware and software, memory, and a data storage unit that contains a set of rules to which patient data 12 is applied. The processor and associated software within predictor module 28 compares the data record for each patient against a set of pre-defined rules and guidelines and presents, as an output, a preliminary patient encounter summary report 30, which may be presented to a physician or staff member via, for example, a user interface that is readable by the physician or his or her staff. For example, if a 35-year old female patient is complaining of a sore throat, excessive coughing, and difficulty in swallowing, predictor module 28 searches its stored rules and compares them to the given symptoms as well as the other patient data 12 to determine a possible assessment. Predictor module 28 does not only consult specific patient data 12 about the patient that is being examined to provide an assessment, but may also consult patient data 12 for other patients. For example, predictor module 28 may consider other 35-year old female patients exhibiting similar symptoms.

In addition to the patient's symptoms, additional patient information 12 may be needed to render and assessment such as the patient's past medical history (have these symptoms being diagnosed in the past?), personal habits (is the patient a smoker, or does the patient exercise enough? or is the patient under great stress?). Predictor module 28 may provide the preliminary patient encounter summary report 30 in a number of forms. The preliminary patient encounter summary report 30 may be in paper report format, or in electronic form and presented as an preliminary patient encounter summary report 30 that can be viewed by the physician or his or her staff on a computer, or wireless hand-held device. Access to the preliminary patient encounter summary report 30 can also be made available via the Internet, thus allowing the physician to access the summary assessment report via a secure access code when away from the office via a web browser or the like.

Preliminary patient encounter summary report 30 can be provided and displayed to a physician on, for example, a hand-held device that the physician can carry with them into the patient's waiting area. The hand-held display allows the physician to review and revise the information on the preliminary patient encounter summary report 30. Included in the preliminary patient summary report 30 is predicted activity, which might include, for example, prescribed medication, a suggested diagnosis, suggested lab tests, or other types of activity. The predicted activity is generated as part of the summary report 30 based on the patient data 12 inputted into system 10. Patient data 12 is compared to the stored set of rules, and predictor module 28 generates the predicted activity for the patient.

Preliminary patient summary report 30 is presented to the physician for editing. Thus, the physician can provide input variables 32, which allows the predictor activity displayed on the preliminary patient encounter summary report 30 to be altered. For example, if preliminary encounter summary report 30 suggests that a strep throat test be administered but did not suggest any other type of test, the examining physician may add another test that he feels the patient should undergo. Further, if preliminary encounter summary report 30 does not prescribe any medication, the physician may feel that certain medication be prescribed. These alterations to preliminary patient encounter summary report 30 could be based upon certain patient data 12 (i.e., patient symptoms, patient's age, patient's prior history) or upon the reviewing physician's or the medical practice's standard procedures.

If the physician wants to alter the information on preliminary patient encounter summary report 30, he or she would then make these changes by entering the information 32, altering preliminary patient encounter summary report 30 and resulting in a revised encounter summary report 34. This revised report 34 includes new recommended activity for that patient. Thus, the inclusion of input variable 32 to preliminary patient encounter summary report 30 results in a revised encounter summary report 34, with new predicted activity. If preliminary patient encounter summary report 30 is presented in electronic form as a summary screen to a hand-held electronic display device for example, the physician edits the information on the screen via any standard method including a wand that updates a touch screen.

When either preliminary encounter summary report 30 or revised encounter summary report 34 is submitted to the system 10, a number of events can occur. The information on encounter summary report 30 including the predicted activity or the information on the revised report 34, including the updated predicted activity, is forwarded electronically to rules engine 36. Also, at this time, a series of actions may be invoked by system 10 based upon the information on either summary report 30 or revised report 34. For example, a series of administrative functions 38 and financial functions 48 can occur, such as the production of a physician note 40, which could be in the form of annotations or reminders to the physician for future visits by this particular patient, or the preparation of a referral letter 42 to another physician. At this stage, other events can occur such as the preparation of a prescription 44, the giving of specific orders 46 such as tests, the processing of the patient's payment 50, providing updates to the patient's medical history stored in a shared health network, national database, or HIE 52, sending a claim 54 to the insurance company, and issuing a patient statement 54. The aforementioned tests can be defined, within the context of this specification, as anything that can be accomplished under a Computerized Physician Order Entry ("CPOE") such as laboratory reports, ultrasounds, imaging, endoscopy, biopsies, genetic tests, non-invasive tests, medical screening tests, and the like.

In addition to the initiation of these events, system 10 submits the information on either the preliminary encounter summary report 30 (if no physician edits 32 were made to the predicted activity) or on the revised encounter summary report 34 (if physician edits were made to the predicted activity) to rules engine 36. Rules engine 36 receives the information and uses algorithms to determine if the stored rules need to be updated to reflect the new information. For example, changes made by the physician to the predicted activity of encounter summary report 30 results in updated predicted activity (i.e., the issuance of a medication X when a 30+ year old patient who is an habitual smoker is complaining of a sore throat). Depending upon how often this occurs, rules engine 36 may recognize a pattern based on the frequency of this occurrence. This may not occur at the first instance the physician prescribes the medication, but might occur after several occurrences. When a pattern is recognized or a threshold is reached, rules engine 36 will update its rule regarding 30+ year old patients who are habitual smokers and who complain of a sore throat, to now recommend that medication X be included in the predicted activity the next time a patient with those symptoms, age and traits visits the medical facility. These adjusted rules are sent from rules engine 36 to predictor module 28. Thus, rules engine 36 "learns" when it recognizes frequent patterns that it receives from the updated predicted activity in updated encounter report 34.

As discussed above, rules engine 36 updates the stored rules when it recognizes a pattern of activity (or updated predicted activity) within preliminary encounter summary report 30 and revised summary report 34. Within this specification, the term "pattern of activity" is used broadly and may include a number of analysis techniques that rules engine 36 uses to determine if the existing rules need to be revised. These techniques may include the reaching of a certain threshold, or other statistical recognition algorithms. Advantageously, rules engine 36 is not limited only to recognizing patterns that occur when the same physician makes repeated changes to the predicted activity. Rules engine 36 may also recognize a pattern of activity with regard to the medical practice itself, which include more than one physician, or recognize patient patterns.

Figure 2:
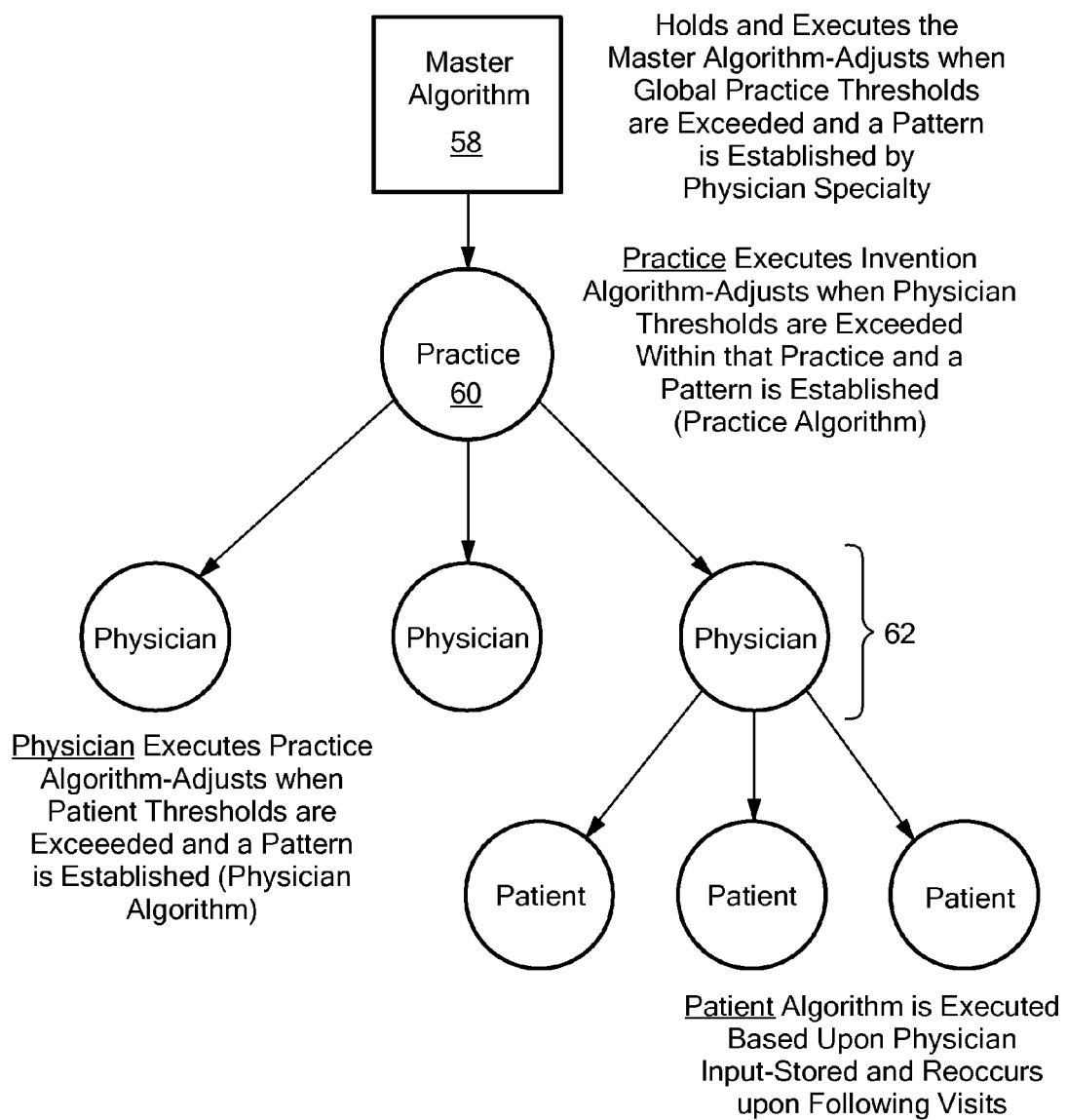
FIG. 2 is an exemplary flow diagram illustrating the different levels at which automated functions may occur in accordance with the principles of the present invention.

FIG. 2 shows an exemplary embodiment of the invention where the stored rules may be changed at different stages in the patient visitation process due to the recognition, by rules engine 36, of a specific pattern of activity. A master algorithm 58 is stored and is used initially by predictor module 28. Thus, for a particular medical practice, system 10 will utilize master algorithm 58 until a pattern of medical practice activity is recognized. Rules engine 56 may recognize a certain pattern of activity occurring within the medical practice, and not necessarily by one physician in that practice. For example, if physician A prescribes medication X for a certain patient condition, and physicians B and C within the practice also prescribes medication X for that same patient condition, rules engine 36 considers this a practice-based predicted updated activity and may alter its rules accordingly. A change in rules at this level results in a revision to master algorithm 58, leading to practice-based rules 60 because the pattern recognized by rules engine 36 was recognized at a practice-level (occurring when physicians A, B, and C all prescribed the same medication for the same patient condition).

System 10 will use the practice rules 60 until rules engine 36 recognizes patterns occurring at the physician level 62. In this example, a pattern of activity is recognized by the behavior of one physician within a practice. For example, physician C within the practice may consistently recommend a virus test, and a week of bed rest for patients over the age of 50 complaining of fatigue and dizziness. In this instance, system 10 might provide a set of rules for each physician, depending upon each physician's tendencies. Thus, physician-based rules 62 may be applied for each physician in a particular medical practice. Thus, for each patient, rules engine 36 applies rules that may have changed due to occurrences at a practice level 60 or at a physician level 62.

Thus, the repeated pattern of physician recommendations might result in rules engine 36 updating the stored rules for each physician such that the next time predictor 28 receives data for a patient over the age of 50 complaining of fatigue and dizziness, and arrives at the doctor's office to visit physician C, predictor module 28 will generate an encounter summary report 30 that now includes in its predicted activity, a virus test, and one week of bed rest for that patient. Thus, rules engine 36 recognizes activity patterns at the practice level and at the physician level and can update its rules for the practice or per each individual physician within the practice. Rules engine 36 can also recognize patterns that occur related to patient information. For example, rules engine 36 might determine that habitual smokers over the age of 50 exhibit other symptoms such as fatigue and that this occurs most with those patients having a family history of depression. Upon determining that the existing stored rules and algorithms need to be revised, the rules and algorithms are adjusted and forwarded to predictor module 28 for subsequent patient visits.

Figure 3A:
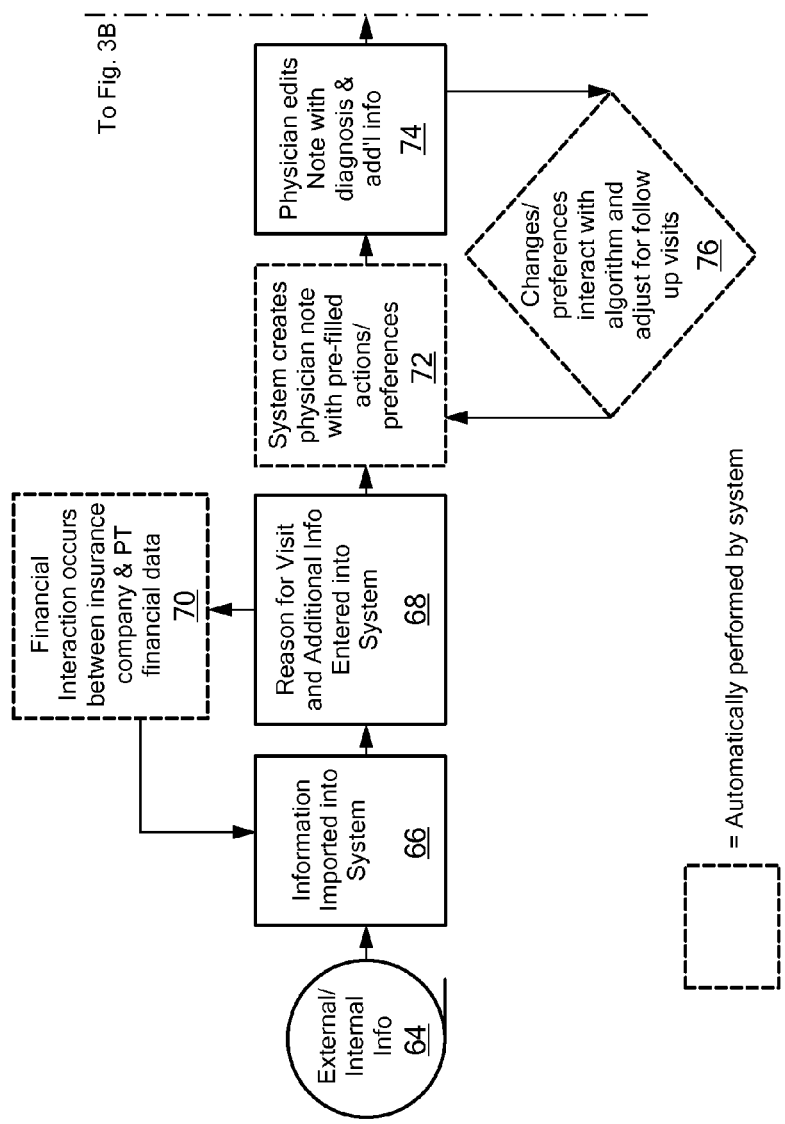
FIG. 3A is the first portion of a flowchart of an exemplary process performed by the patient encounter report updating system of the present invention.
Figure 3B:
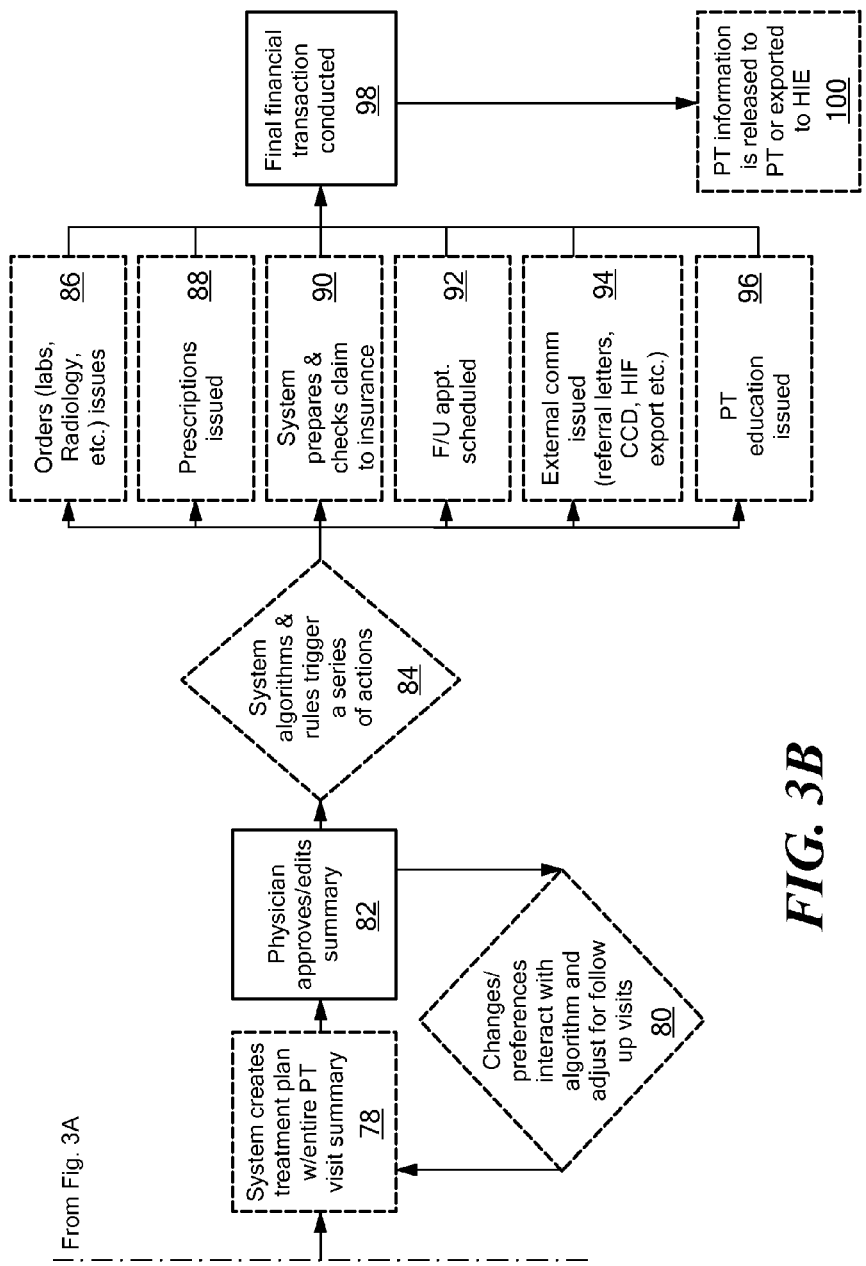
FIG. 3B is the second portion of a flowchart of an exemplary process performed by the patient encounter report updating system of the present invention

FIGS. 3A and 3B represent an exemplary flow diagram showing the steps by an embodiment of the present invention. FIGS. 3A and 3B illustrate how the present invention interacts with external data and inputs to provide a system that automatically updates patient summary encounter reports based on recognized patterns of practice, physician, and patient occurrences. Patient information 64 of the type described above with respect to FIG. 1 is obtained. If the patient is visiting the medical facility for the first time, the information 64 can be obtained from the patient directly via a written form or from other external patient sources, such as their email or downloaded from a website. Alternately, the information can be obtained from an outside record-keeping source. Once this information 64 is obtained, it is stored and tagged to the patient for future visits. Information 64 is imported, via step 66, and stored along with other related patient information such as the reason for the patient's visit, and the patient's financial and medical history, via step 68. All of this information is stored and made available to predictor module 28.

System 10 then extracts the patient's financial and insurance information, which may include credit history and their insurance carrier. System 10 is in communication with the patient's insurance carrier and financial institution and determines if the patient is covered for medical procedures. Thus, there is an interaction, via step 70, between system 10 and outside sources to assure that the patient can proceed with their visit. System 10 then creates a preliminary patient encounter summary report at step 72, that includes physician notes with prefilled actions and preferences ("predicted activity"). These actions are generated by predictor module 28 by analyzing the patient's stored data and symptoms, and comparing this information 64 to a set of stored rules. These rules may include tendencies by each physician within the practice including treatment plans, prescriptions and other post-visit activities, tendencies by the practice as a whole, tendencies and standards obtained from other, third party medical practices, and medical journals, and patient tendencies. Patient tendencies may include information about other patient's within the practice that may have, for example, similar symptoms or medical histories, or from patients outside of the medical practice. The stored rules may be updated, depending upon decisions by rules engine 36.

A physician can edit and update the information in the preliminary patient encounter summary report, via step 74. The predicted activity on the preliminary encounter summary report may include a diagnosis of the patient's illness, prescription, recommended lab tests, and further recommendations. The physician can edit this activity by, for example, changing or eliminating the suggested prescription or lab test, offering a different diagnosis, or adding other notes and suggestions. Any changes to the preliminary patient encounter summary report automatically interact with the stored rules and rules engine 36, via step 76. If rules engine 36 recognizes a pattern and determines that a change to one or more stored rules is necessary, it automatically creates a new set of rules that will result in a new preliminary patient encounter summary report the next time the patient visits, or for other patient exhibiting similar symptoms and patient characteristics.

Referring now to FIG. 3B, once the physician has edited the preliminary encounter summary report, at step 74, the system 10 incorporates these edits into an updated encounter summary report containing an entire visit summary and predicted activity for the patient, at step 78. The physician can continue to edit the encounter summary report, at which time rules engine 36 will continue to update the rules and adjust future encounter summary reports for future visits, at step 80. One the physician approves the final encounter summary report, via step 82, a series of events are triggered, at step 84. These events can include at least those shown in FIG. 3B including laboratory tests 86, the issuing of medical prescriptions 88, the checking of insurance claims 90, scheduling follow up visits 92, issuing referral letters or communications to outside entities 94, informing the patient about the diagnosis and providing medical advice and educational tips 96, generating financial transactions such as finalizing payment 98, and releasing patient information to outside entities 100. At this time, rules engine 36 receives the approved preliminary patient encounter summary report 30 with predicted activity or the revised summary report 34 with updated predicted activity. In one embodiment, one or more of these events can occur automatically upon the submission of either the preliminary patient encounter report or the updated encounter summary report.

The initiating of the above events can be performed by an event generating module, which can include various hardware and software modules within the system. For example, upon the triggering of an event, the address of a laboratory used by the practice is retrieved, and the system sends an electronic lab request for the patient, to the lab. Or, a prescription can be automatically generated and sent via, for example, electronic mail, to the pharmacy near where the patient lives. In other scenarios, an email to the patient's insurance company can be generated or a referral letter sent to another physician.

Several examples of how system 10 operates are now provided. USE CASE 1: This scenario represents the system's a first-time encounter with a patient without previous patient specific data 14.

STEP 1: Patient A is scheduled for an appointment on Dec. 1, 2009. Patient A is a first time patient with this specific medical practice. Patient A gives sore throat as reason for appointment. Patient A's initial demographics and medical profile are captured over the phone, web portal or via an external third party source (e.g., Health Information Network) and may include but is not limited to name, gender, health insurance, date of birth, phone number, pertinent past medical history, etc). Predictor module 28 then (a) analyzes demographic pattern (age, gender, etc), (b) analyzes the reason for the patient's visit (sore throat), and (c) analyzes pertinent past medical history for that patient.

STEP 2: Patient A arrives for her appointment on Dec. 1, 2009. Predictor module 28 uses steps (a), (b), and (c) above to formulate an activity list. This might include insurance eligibility, which is automatically checked and co-pay information captured and debited (credit card information previously captured). A list of physician predicted activity may then be created and presented in any format to the physician. One format is to display the predicted activity in the form of a preliminary patient encounter summary report on a screen of a computer, such as a hand-held computing device. The summary report may include a full Subjective Objective Assessment and Plan ("SOAP"). The following is an exemplary sample output that is presented to the physician:

Patient A presents today for sore throat. Patient is a 35-year-old female in no acute distress. Sore throat is characterized as being constant, hard to swallow and is usually associated with coughing.
≦More dynamically generated text≧
Social History
Patient has does not smoke or drink alcohol excessively.
≦More dynamically generated text≧
Assessment:
  Acute Pharyngitis
Plan
Strep throat test administered/ordered. X, Y, Z medications to be prescribed. Patient is to return in 2 weeks STEP 3: Physician A examines the patient. The physician reviews the predicted activity information, approves as is, and submits it to system 10, without edits. Post encounter activity and orders are then generated.

STEP 4: When the physician approves the predicted activity information, other actions take place. For example, a final document is created, secondary financial information is processed, charges for strep throat and other encounter events are generated. If financial responsibility is with the patient (the system 10 would know this in advance due to a prior eligibility check by system 10), automatic payment is performed. Other additional external documentation may be created such as the issuing of a prescription for medication X,Y, orders for strep throat lab work, the scheduling of a follow-up visit in two weeks, or the preparation of a referral letter to another doctor. Medical billing actions can also be taken such as the issuance of an insurance claim. These steps can be performed electronically or via paper, i.e., mailing and facsimile.

STEP 5: Rules engine 36 then performs a run-through of the entire encounter to "learn" and, if necessary, change stored rules, depending on recognized patterns of events, for future use.

USE CASE 2: This scenario represents the system's a first-time encounter with a patient without previous patient specific data 14, but in this scenario, system 10 incorporates physician edits and rules engine 36 in conjunction with predictor module 28 provides an updated set of predicted activities.

STEP 1: Patient A is scheduled for an appointment on Dec. 1, 2009. Patient A is a first time patient with this practice. Patient A gives sore throat as reason for appointment. Patient A's initial demographics and medical profile are captured over the phone, web portal or via an external source. Predictor module 28 then (a) analyzes demographic patterns (age, gender, etc); (b) analyzes reason for visit (sore throat); and (c) analyzes pertinent the patient's past medical history.

STEP 2: Patient A arrives for her appointment on Dec. 1, 2009. Predictor module 28 uses steps (a), (b), and (c) above to formulate an activity list. Again, this might include insurance eligibility which is automatically checked and co-pay information that is automatically Physician predicted activity information is then generated and presented. A sample SOAP output is as follows:

Patient A presents today for sore throat. Patient is a 35-year-old female in no acute distress. Sore throat is characterized as being constant, hard to swallow and is usually associated with coughing.
≦More dynamically generated text≧
Social History
Patient has does not smoke or drink alcohol excessively.
≦More dynamically generated text≧
Assessment:
  Acute Pharyngitis
Plan
Strep throat test administered/ordered. X, Y, Z medications to be prescribed. Patient is to return in 2 weeks.
1. Post encounter activity and orders are also generated.
  Example:
  Prescription.
  Referring Physician
  Orders
  Pt Education
  Other pertinent info
  Financials and Claims STEP 3: The physician (i.e., "Doctor A") examines the patient and then revises the predicted activity resulting in the following:
1. Example output: (edits are shown in CAPITALS)
   Patient A presents today for sore throat. Patient is a 35-year-old female in no acute distress. Sore throat is characterized as being constant, hard to swallow and is usually associated with coughing.
   ≦More dynamically generated text≧
   Social History
   Patient is A HABITUAL SMOKER, SMOKING 2-3 PACKS PER DAY. Patient does not drink alcohol excessively.
   ≦More dynamically generated text≧
   Assessment:
   Acute Pharyngitis
   Plan:
   Strep throat test administered/ordered. X VIRUS TEST ORDERED. X, Y MEDICATIONS to be prescribed. Patient is to return in 2 weeks.
2. Doctor A also reviews below:
   Prescription OK.
      ADDED X, Y MEDICATIONS
   Referring Physician OK.
   Orders OK
      ADDED X VIRUS TEST
   Financials OK
   Follow up Appointment OK
   Patient Education Topic OK
   Other pertinent info STEP 4: Rules engine 36 analyzes the above edits for future use. STEP 5: One or more of the previously-listed actions take place (i.e., creating final documents, processing secondary financial information, initiating charges for strep throat, obtaining payment, etc.). STEP 6: Rules engine 36 then runs analyzes the contents of the entire encounter to determine if any patterns have arisen.

USE CASE 3: This use case is performed after Use Case 2, where now a different patient, i.e., Patient B, has a first time encounter with system 10 and is examined by a different physician (i.e., "Doctor B").

STEP 1: Rules engine 36 performs an analysis of the patient encounter to "learn" for future use on different patients, i.e. Patient A (Use Case 2). In this scenario, rules engine 36 has determined that at the Practice level, 90% of recent encounters with a "sore throat" have added "X,Y medications" and have added orders for "X virus test", however "a habitual smoker, smoking 2-3 packs per day" remains at the Patient level. Predictor module 28 revises its predicted activity according to instruction from the rules engine 36.

STEP 2: Patient B is scheduled for an appointment on Dec. 2, 2009. Patient B is a first-time patient with this particular medical practice. Patient B gives "sore throat" as reason for appointment. Patient B's initial demographics and medical profile are captured over the phone, web portal or via an external information source. Predictor module 28 then (a) analyzes demographic pattern (age, gender, etc); (b) analyzes reason for visit (sore throat); and (c) analyzes pertinent past medical history.

STEP 3: Patient B arrives for her appointment on Dec. 2, 2009. Predictor module 28 uses information from steps (a), (b), and (c) above to formulate an activity list and in doing so recognizes a pattern from Patient A due to Patient A's past visits. Insurance eligibility is automatically checked and co-pay information captured and debited (credit card information previously captured). The physician's predicted activity is created and displayed in a screen using the logic from rules engine 36. The predicted activity includes a full SOAP including, as an example, the following output (new predicted activity is in CAPITALS):
   Patient B presents today for sore throat. Patient is a 35 year old male in no acute distress. Sore throat is characterized as being constant, hard to swallow and is usually associated with coughing.
   ≦More dynamically generated text≧
   Social History
   Patient has does not smoke or drink alcohol excessively.
   ≦More dynamically generated text≧
   Assessment:
   Acute Pharyngitis
   Plan:
   Strep throat test administered/ordered.
   X VIRUS TEST ORDERED.
   X, Y MEDICATIONS TO BE PRESCRIBED.
   Patient is to return in 2 weeks.
   Doctor B also reviews below information:
   Prescription OK.
   Referring Physician OK.
   Orders OK
   Financials OK
   Follow up Appointment OK
   Patient Education Topic OK
   Other pertinent info
   Financials OK.

Thus, system 10 has now incorporated the updated predicted activity entered for Patient A (X virus test ordered, and X, Y medications to be processed) into the predicted activity for Patient B. This was done due to the recognition by rules engine 36 of a pattern exhibited by the medical practice (Doctor A examined Patient A in the first instance, while Doctor B examines Patient B in this instance). This change in the stored rules is identified as a practice-based change 60 (see FIG. 2).

STEP 4: Doctor B examines Patient B. Doctor B reviews the predicted activity information, approves as is, and submits it. Post encounter activity and orders are generated as described with respect to earlier use cases. At this time, other actions may take place. Final documents are created. Secondary financial information is processed. Charges for strep throat are created. If financial responsibility is on the patient, automatic payment is performed. Additional external documentation is also created such as a prescription for Medication X,Y and orders for strep throat lab work to be one on Patient B. These events were due to the updated predicted activity that rules engine 36 recognized for Patient A. Other events such as a referral letter to the doctor/entity that sent this patient, medical billing, and insurance claim submission are performed at this time. STEP 5: Rules engine 36 analyzes Doctor B's edits to the predicted activity and also analyzes any other events that occurred for Patient B's encounter to "learn" for future use.

USE CASE 4: This scenario covers a patient's second time encounter with system 10.

STEP 1: Patient Mary Doe is scheduled for an appointment on Dec. 17, 2009. Mary Doe was last seen Dec. 1 2009 by Dr. James Smith within the same medical practice. Mary Doe gives "follow-up appointment for sore throat" as reason for her appointment. Mary Doe's initial demographics were already captured in the previous visit by system 10. Predictor module 28 then (a) analyzes the demographic pattern (age, gender, etc); (b) analyzes the reason for the visit (sore throat follow up); and (c) analyzes past encounters for this patient (sore throat).

STEP 2: Patient Mary Doe arrives for her appointment on Dec. 17, 2009. Predictor module 28 uses steps (a), (b), and (c) above to formulate a task list. Mary Doe's insurance eligibility is automatically checked and co-pay information captured and debited. A preliminary encounter summary report is created using the logic of rules engine 36. A full SOAP is generated that includes the following:

Mary Doe presents today for follow up visit following a sore throat. Patient is a 35-year-old female in no acute distress. Sore throat has improved with little to no recurrence.

≦More dynamically generated text≧

Social History

Patient is a habitual smoker, smoking 2-3 packs per day. Patient does not drink alcohol excessively.

Medications X, Y

≦More dynamically generated text≧

Assessment:

Acute Pharyngitis resolved

Plan:

Return as needed.

STEP 3: Doctor James Smith examines patient Mary Doe. Doctor Smith reviews the preliminary document and makes no edits, as everything was normal and filled correctly as per her last visit. As described above with respect to other scenarios, post-encounter activity and orders are generated.

STEP 4: Rules engine 36 receives a lack of edits and notes this for future use. STEP 5: Other post-encounter events take place as described in earlier scenarios. STEP 6: Rules engine 36 performs an analysis of the entire encounter to "learn" for future use.

Thus, the present invention represents a dynamic method of automatically processing patient visits by analyzing patient encounters at a medical practice, recognizing patterns that emerge due to repeated practice, physician and patient behaviors, and updating a set of defined rules and procedures accordingly such that subsequent patient encounters are analyzed and processed according to the updated set of rules and procedures.

Figure 4:
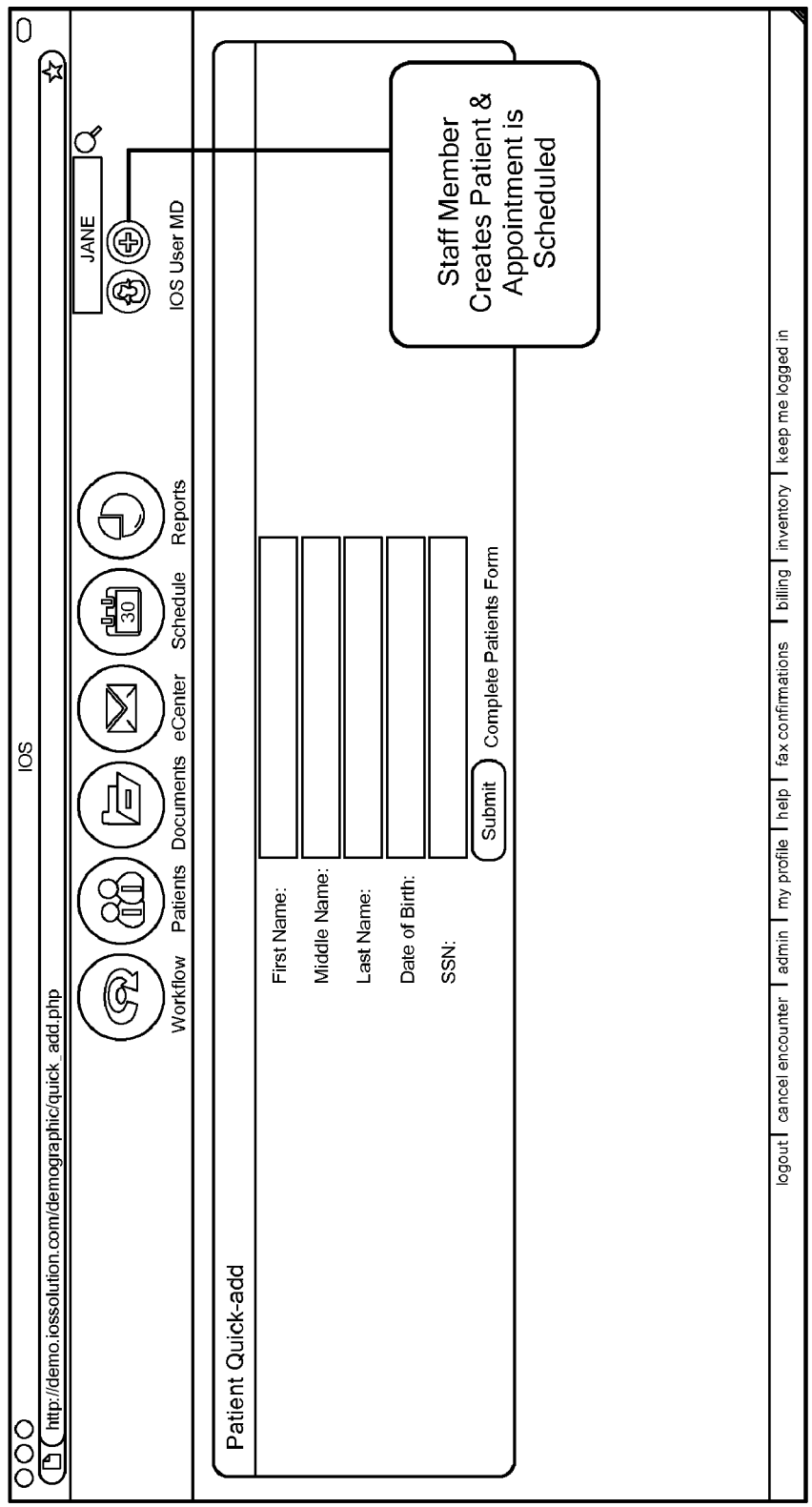
FIG. 4 is a depiction of an exemplary computer screen generated for a patient prior to an initial visit in accordance with the principles of the present invention.
Figure 5:
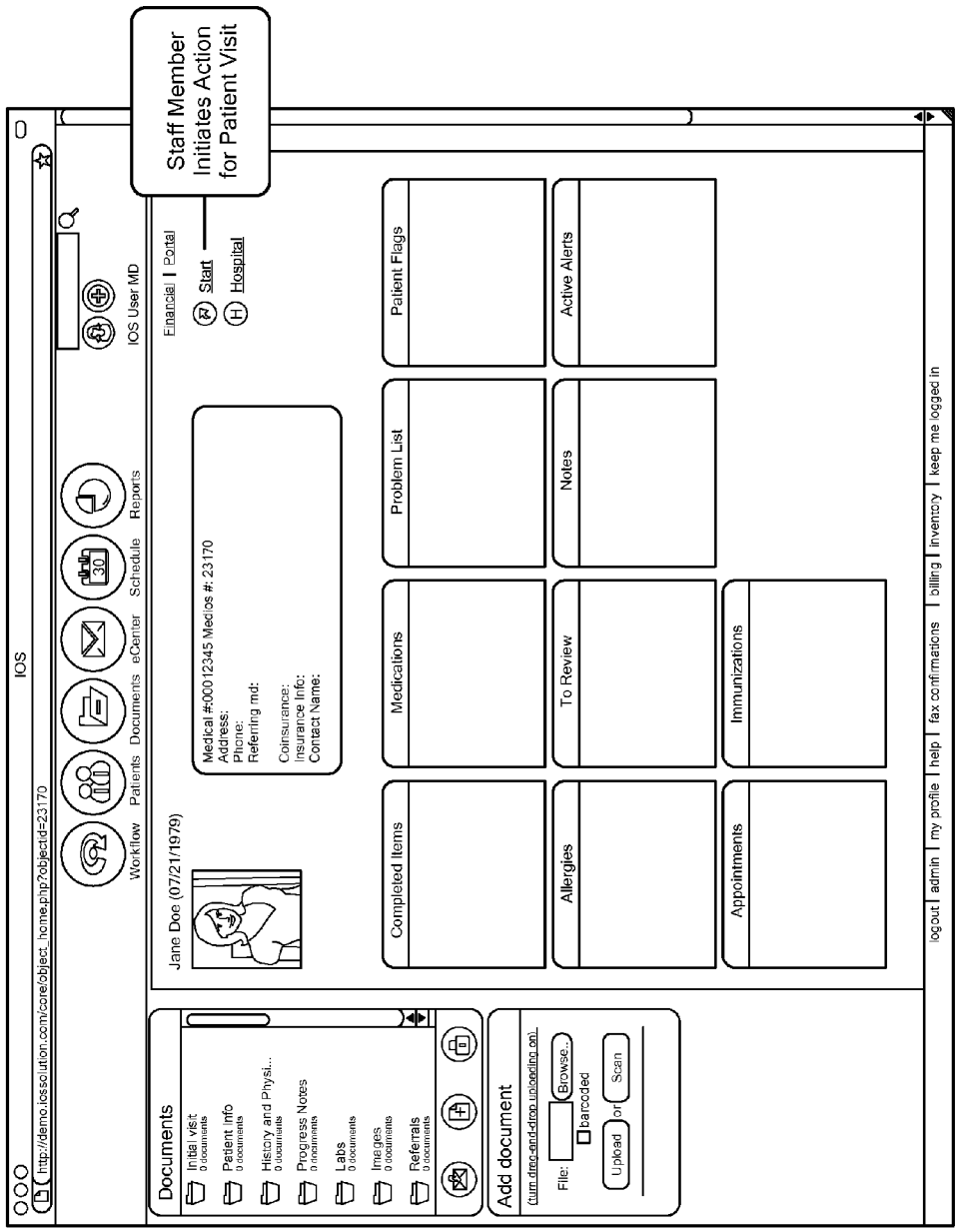
FIG. 5 is a depiction of an exemplary computer screen containing information about a patient in accordance with the principles of the present invention.
Figure 6:
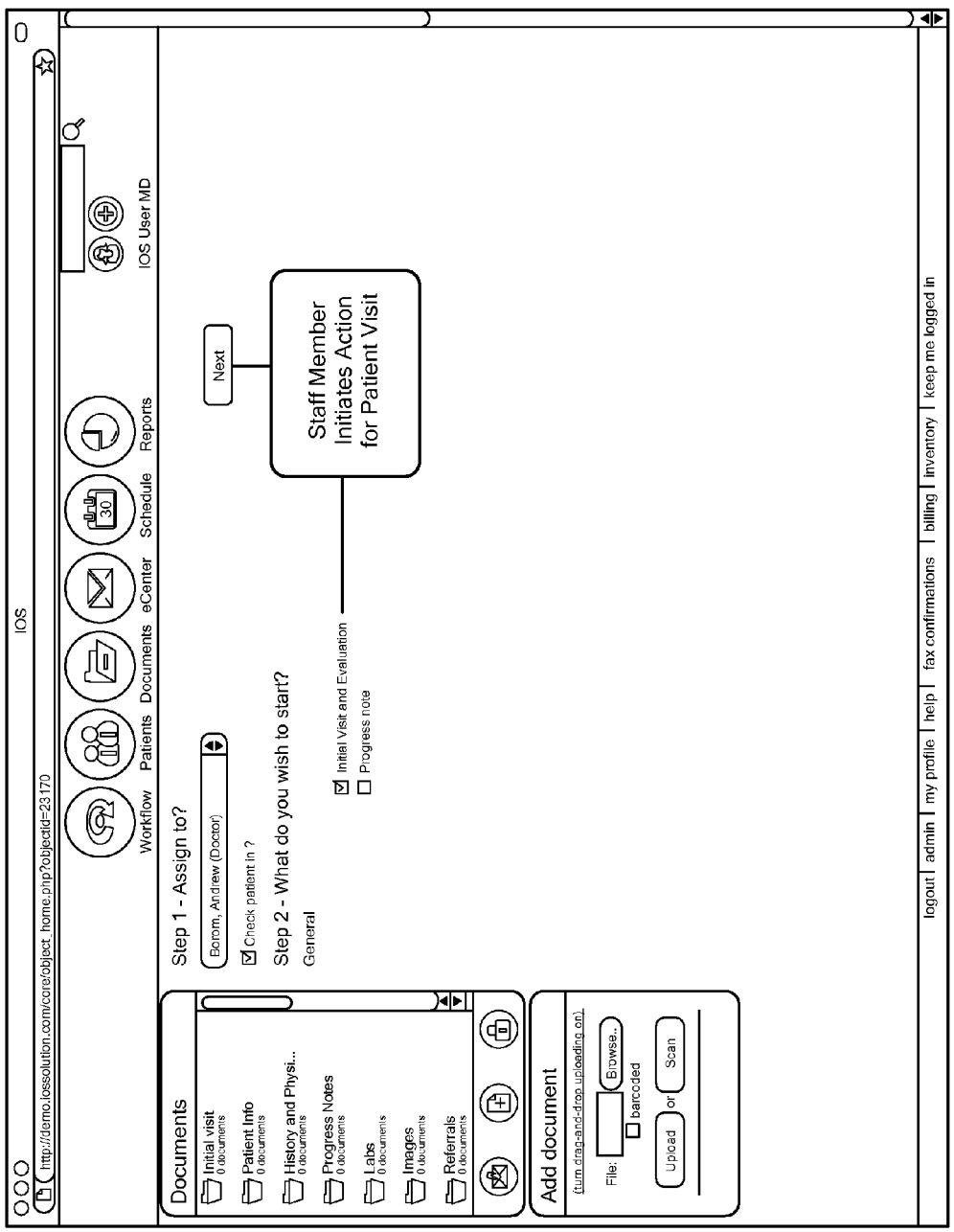
FIG. 6 is a depiction of an exemplary computer screen showing additional information entered for the patient in accordance with the principles of the present invention.

FIGS. 4-14 represent exemplary screen images that may be presented to staff members or physicians using an embodiment of system 10 of the present invention. FIG. 4 represents an exemplary screen presented, for example, to a staff person at a medical facility where a patient is visiting the medical practice for the first time. A new patient profile is created and an initial appointment is scheduled for that patient. As shown in FIG. 5, a profile for a new patient ("Jane Doe") has been created. The patient is given a medical ID number and initiates action for the patient visit. In FIG. 6, the staff member enters the name of the doctor (Dr. Borom) that the patient is to be assigned to, indicates that it is an initial visit and evaluation for the patient, and proceeds with other check-in procedures. Predictor module 28 already has stored the tendencies and recognized patterns for Dr. Borom as well as his medical practice.

Figure 7:
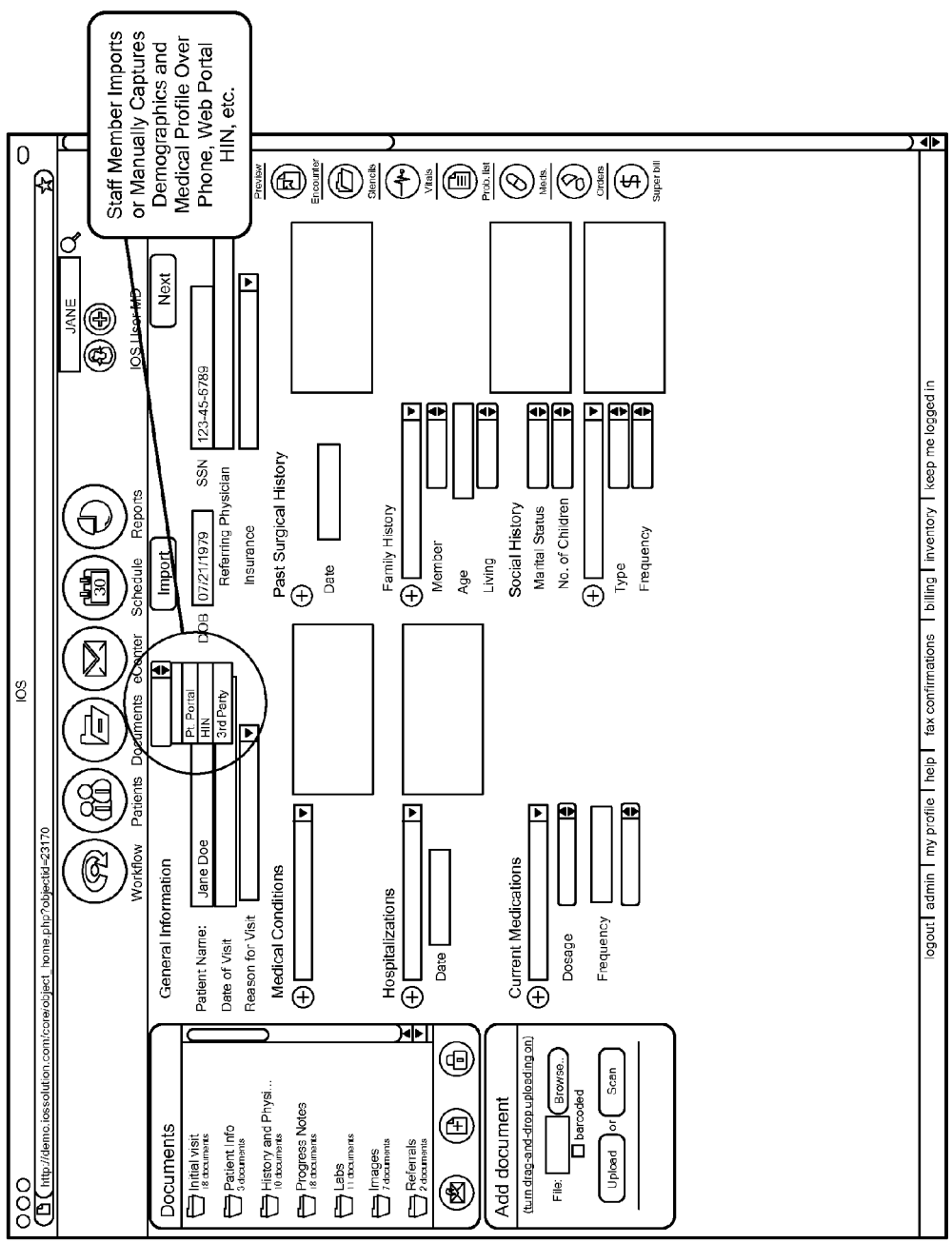
FIG. 7 is a depiction of an exemplary computer screen showing how imported information is obtained regarding the patient in accordance with the principles of the present invention.
Figure 8:
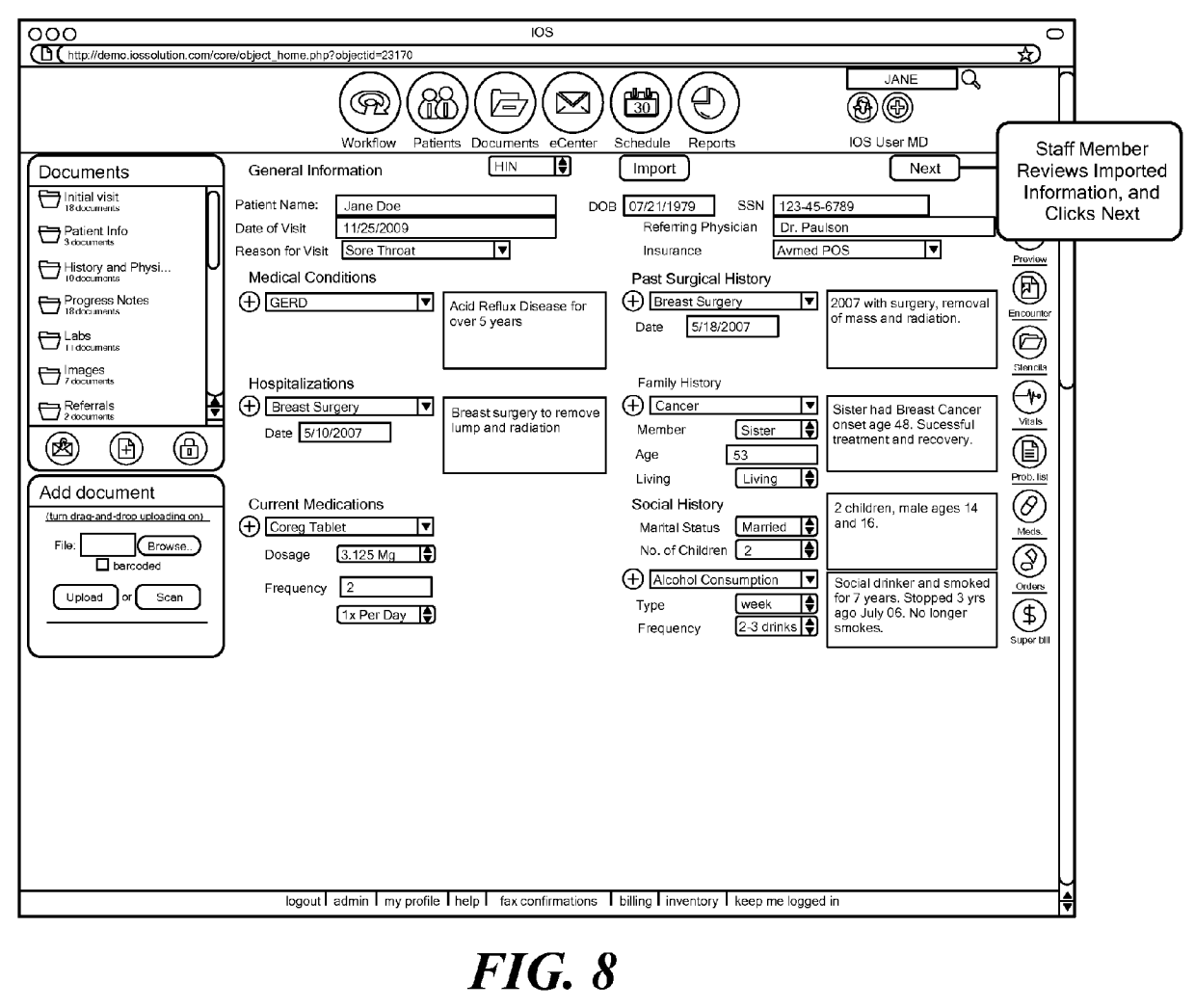

At this point in the check-in process, system 10 retrieves other demographic, medical, and financial information either from the patient directly or via third-party record-keeping entities, as shown in FIG. 7. In FIG. 8, the patient's profile is populated with information such as the reason for the patient's visit, past medical history including prior hospital visits, current medications, past surgical history, referring physician, family medical history and social history.

Figure 9:
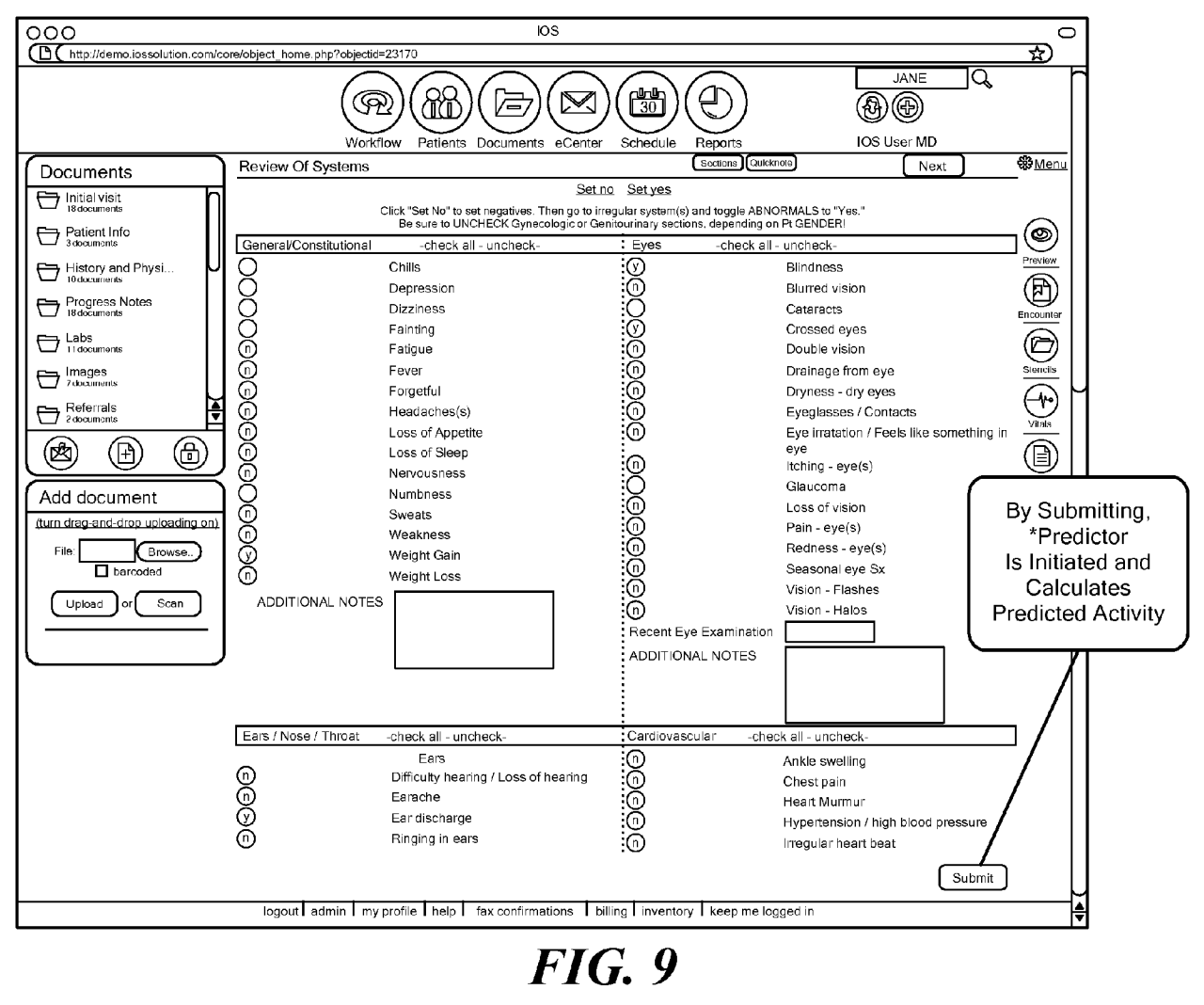

In FIG. 9, a screen representing a review of patient symptoms is presented. A medical staff person can enter one or more patient symptoms. These symptoms, along with the patient's other information, is reviewed, and once confirmed, submitted to predictor module 28 for processing. Predictor module 28 then calculates predicted activity for Jane Doe, and this activity is included in a preliminary patient encounter summary report that is presented, based upon access to the system's stored rules and algorithms, to the physician who will examine the patient.

Figure 10:
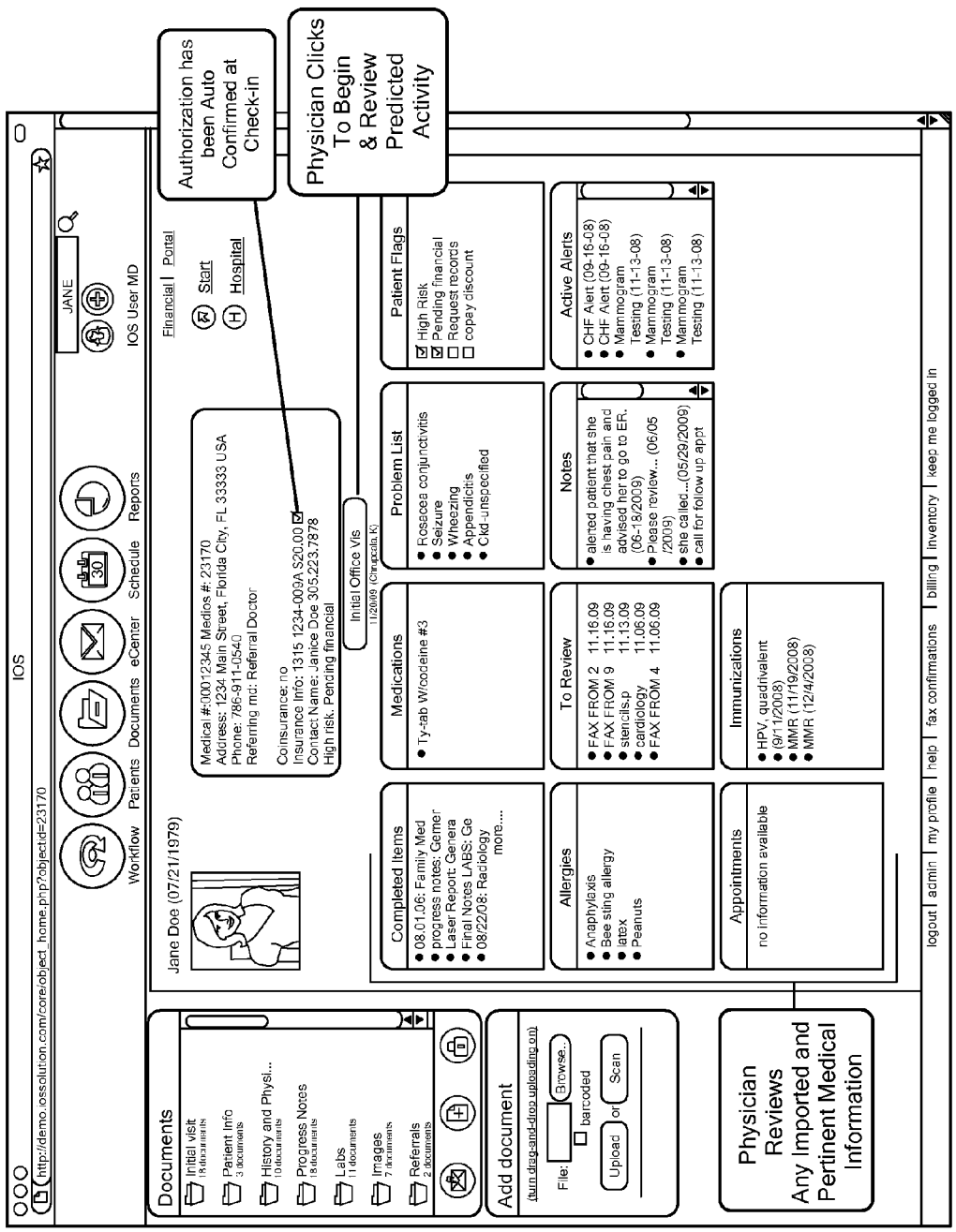
FIG. 10 is a depiction of an exemplary computer screen showing the completed information entered for the patient in accordance with the principles of the present invention.

FIG. 10 is an exemplary screen showing information related to the patient, Jane Doe. The fields have been populated with information obtained from the patient or via outside sources. Each field in the screen can be reviewed and edited. The patient's payment is also recorded as well as her insurance information. System 10 of the present invention can automatically connect to outside sources that provide medical, financial, and personal information about the patient. All edits and updates to the patient's profile are maintained in a database either within the medical facility or in an outside facility.

Figure 11:
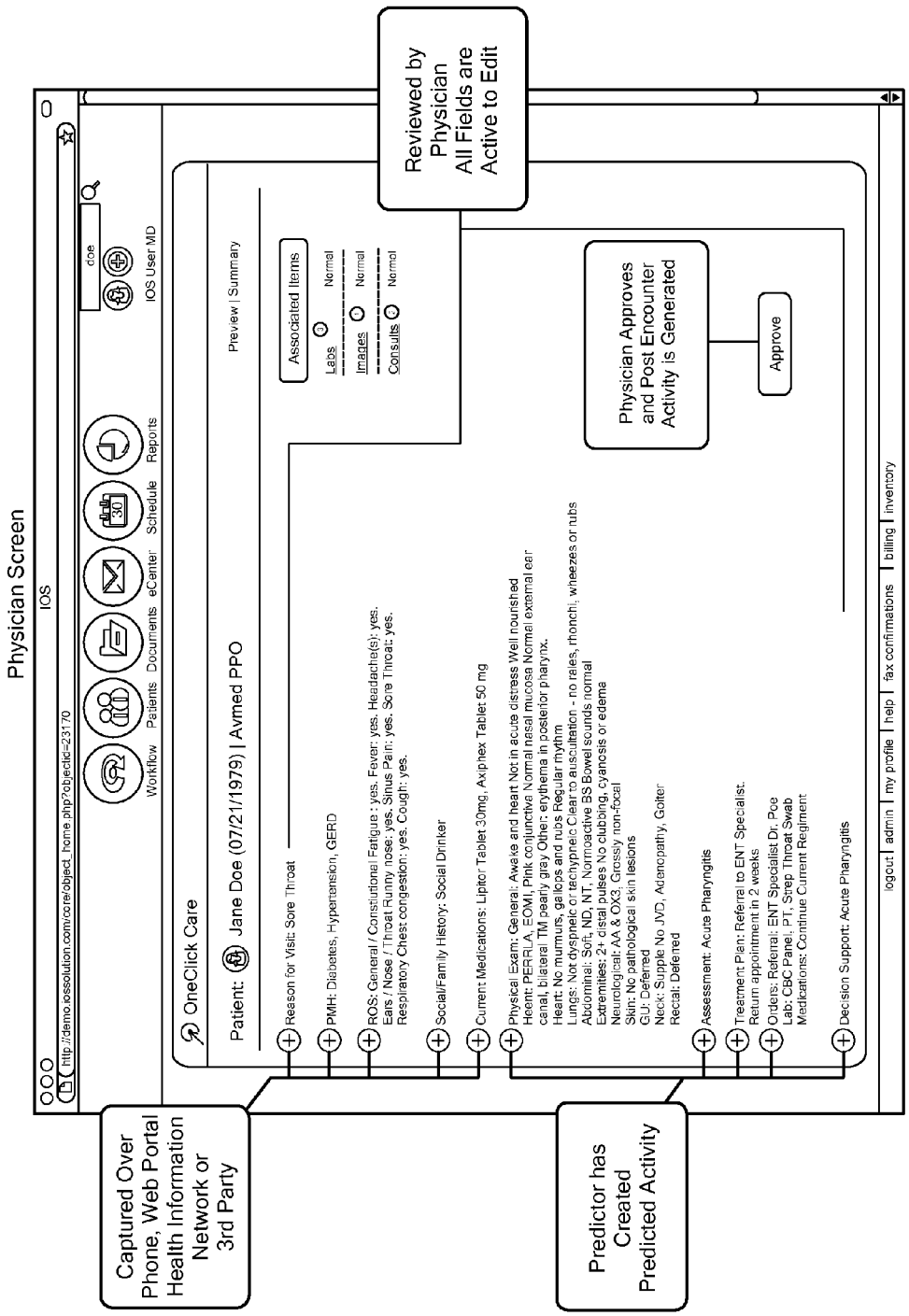
FIG. 11 is a depiction of an exemplary preliminary summary screen for the patient presented to a physician in accordance with the principles of the present invention.

FIG. 11 represents an exemplary screen presented to the physician that is to examine the patient. The screen may be presented to the physician on his or her mobile computing device or personal computer, where the information can be reviewed prior to the patient examination. At this time, predictor module 28 has already analyzed the patient information, compared it to its stored set of rules and algorithms, and has provided a list of predicted activity for this patient encounter. It should be noted that this screen, as well as all the screen images shown in FIGS. 4-14 are merely exemplary and it is within the scope of the invention to present patient data and predicted activity in any readable format, whether the output report is on paper or presented on a computer screen.

Thus, examining the screen shown in FIG. 11, which represents an exemplary preliminary encounter summary report 30, it can be seen that both the patient data that was collected at or around the time of the patient's initial visit, and the predicted activity determined by predictor module 28, are presented to the physician. For example, the patient's reason for their visit (sore throat), previous medical history (diabetes, etc.), symptoms (fatigue, headache, sinus pain, etc.), social and family history (social drinker), and current medications, are all listed for the physician's review. Predicted activity as determined by the predictor module 28 may include an assessment (acute pharyngitis), a treatment plan (refer to ENT specialist, etc.), orders (strep throat swab, etc.) and final diagnosis (acute pharyngitis). Each field shown in FIG. 11 is active and can be reviewed and edited by the examining physician or his staff. By clicking the "Approve" button, the physician is indicating he or she agrees with the information on report 30, without edits.

However, the physician need not agree with the patient data or predicted activity shown in report 30 and may decide to change one or more items. For example, referring to FIG. 12, although predictor module 28 has indicated that Jane Doe is a "social drinker", the physician (or staff member) may want to update or revise this status such as adding the patient's marital status, number of children, and indicate that although the patient used to smoke and drink occasionally for seven years, she stopped three years ago and now no longer smokes. This language can be conveniently added directly to this screen via conventional means such as a wand and touch screen or my other means. All edits to the patient's data fields are automatically recorded and stored so that the system 10 will update and store this information for Jane Doe and will use the updated information for her next visit.

The physician may also want to edit the predicted activity shown on report 30. This can be done in the same way, by clicking on the field to be edited and adding, deleting, or editing the text in that field. For example, the physician may want to prescribe another drug instead of or in addition to the medication indicated by the predictor activity in report 30. Whenever edits to report 30 occur, and a revised encounter summary report 34 is created, rules engine 36 receives them and compares them to the stored set of rules to determine if a pattern exists or if a threshold has been reached. In one embodiment, the determination if a threshold has been reached or a pattern has been detected occurs automatically upon revisions or edits made to the predicted activity on the patient encounter report 30. Thus, in one scenario, when the physician edits the encounter report 30, the system automatically determines if the edits give rise to updated predicted activity that exceeds a predetermined threshold or represents a recognizable pattern when compared to a predetermined standard. Rules engine 36 recognizes patterns occurring at the medical practice level, the physician level, and the patient level.

Figure 12:
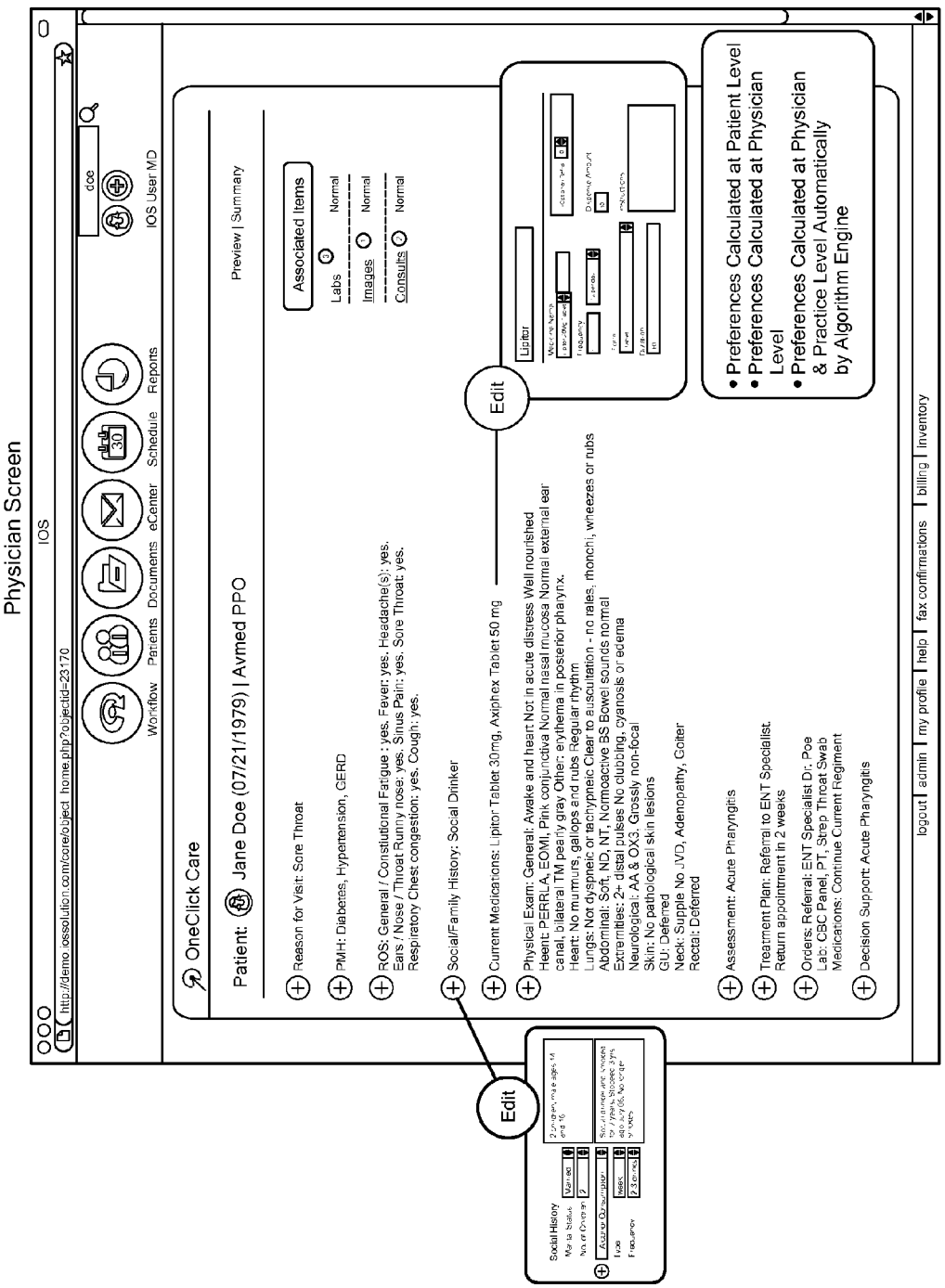
FIG. 12 is a depiction of an exemplary screen allowing a physician to edit the patient's information in accordance with the principles of the present invention.
Figure 13:
FIG. 13 is a depiction of an exemplary detailed summary screen for the patient presented to the physician in accordance with the principles of the present invention.
Figure 14:
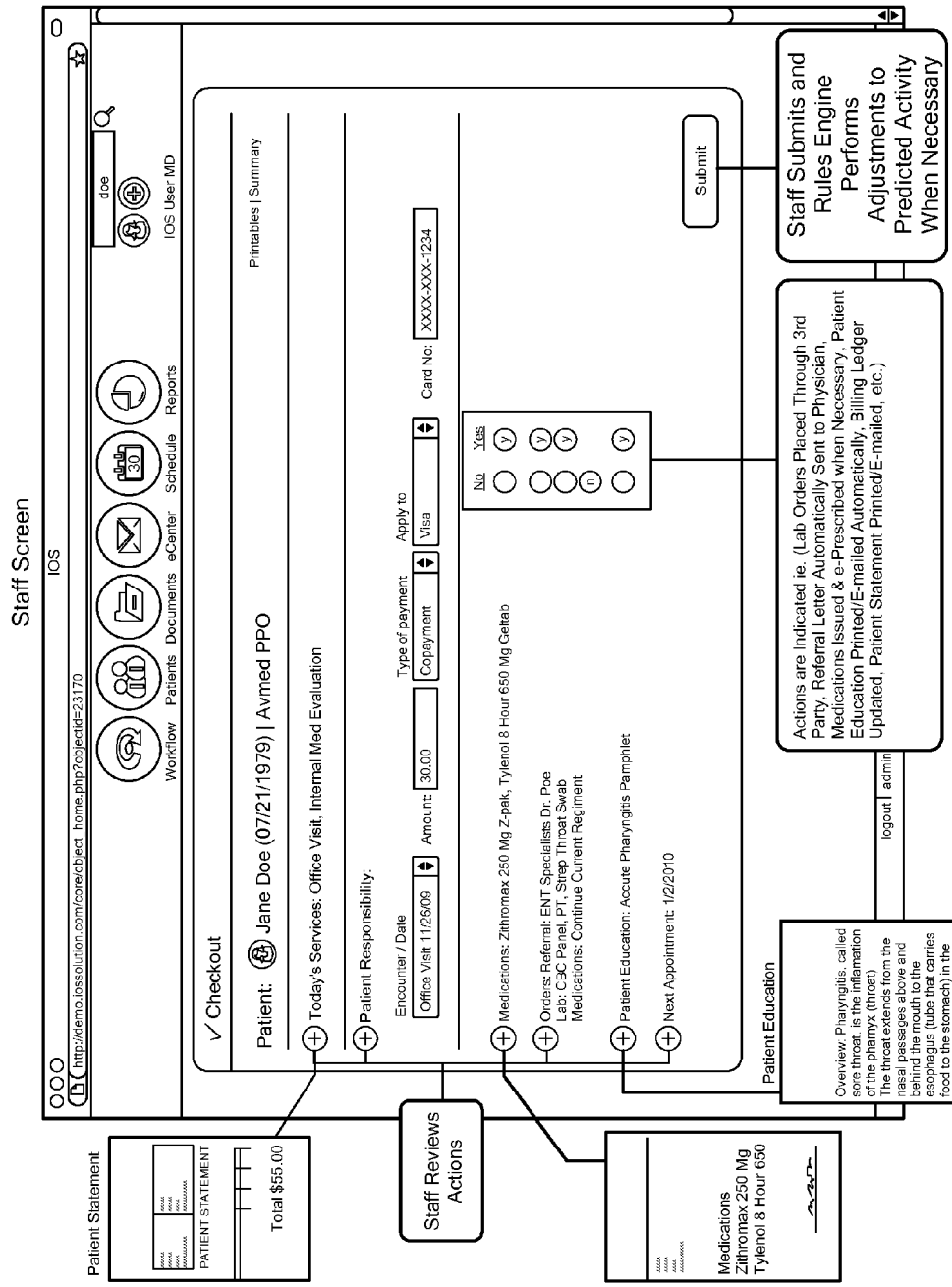
FIG. 14 is a depiction of an exemplary checkout screen for the patient in accordance with the principles of the present invention.

FIG. 13 represents a more detailed physician screen that can be presented, which contains more detail than what is presented in the screen shown in FIGS. 11 and 12. Here, as with the summary screens, the physician can edit the information as he or she sees fit. In FIG. 14, a staff person is presented with a "check-out" screen. The screen summarizes the events of the patient encounter including the diagnosis and medications prescribed or lab tests suggested and confirmation of final payment. Also included are any changes to the predicted activity made by the presiding physician. Theses changes are transmitted to the rules engine 36 where under certain conditions, changes to the stored rules occur and a new set of predicted activities are generated for use by predictor module 28 in subsequent patient visits.

The present invention can be realized in hardware, software, or a combination of hardware and software. Any kind of computing system, or other apparatus adapted for carrying out the methods described herein, is suited to perform the functions described herein.

A typical combination of hardware and software could be a computer system having one or more processing elements and a computer program stored on a storage medium that, when loaded and executed, controls the computer system such that it carries out the methods described herein. The present invention can also be embedded in a computer program product, which comprises all the features enabling the implementation of the methods described herein, and which, when loaded in a computing system is able to carry out these methods. Storage medium refers to any volatile or non-volatile storage device.

Computer program or application in the present context means any expression, in any language, code or notation, of a set of instructions intended to cause a system having an information processing capability to perform a particular function either directly or after either or both of the following a) conversion to another language, code or notation; b) reproduction in a different material form.

In addition, unless mention was made above to the contrary, it should be noted that all of the accompanying drawings are not to scale. Significantly, this invention can be embodied in other specific forms without departing from the spirit or essential attributes thereof, and accordingly, reference should be had to the following claims, rather than to the foregoing specification, as indicating the scope of the invention.

What is claimed is:

1. A method for automatically and iteratively updating patient encounter reports, the method comprising:
storing one or more rules in a tangible, storage medium;
a predictor module applying patient characteristics to the stored rules to produce a preliminary patient encounter report, the preliminary patient encounter report including predicted activity for a patient medical encounter;
presenting the preliminary patient encounter report for editing;
receiving edits to the preliminary patient encounter report;
producing an edited patient encounter report containing updated predicted activity in response to the editing;
a processor determining if the edits to the patient encounter report meet a threshold level; and
a rules engine replacing the stored rules with updated rules based on a result of determining if the edits to the preliminary patient encounter report meet a threshold level
the predictor module applying a subsequent set of patient characteristics to the updated rules to produce a subsequent patient encounter report, the subsequent patient encounter report including predicted activity for a subsequent patient medical encounter.

2. The method of claim 1, further comprising automatically generating at least one action upon submission of the edited patient encounter report.

3. The method of claim 2, wherein the at least one action includes one or more of generating a referral letter, issuing a medication prescription, generating financial transactions, and ordering tests.

4. The method of claim 1, wherein determining if the edits to the patient encounter report meet a threshold level includes determining if a threshold level has been met at a physician level.

5. The method of claim 1, wherein determining if the edits to the patient encounter report meet a threshold level includes determining if a threshold level has been met at a healthcare facility level.

6. The method of claim 1, wherein determining if the edits to the patient encounter report meet a threshold level includes determining if a threshold level has been met at a patient level.

7. The method of claim 1, wherein determining if the edits to the patient encounter report meet a threshold level occurs automatically when the editing of the patient encounter report occurs.

8. A system for automatically and iteratively updating patient encounter reports comprising:
a tangible storage medium for storing patient characteristics and one or more stored rules;
a predictor module comprising a central processing unit (CPU), a computer-readable memory, and a computer-readable, tangible data storage device for applying the patient characteristics to the one or more stored rules to produce a patient preliminary encounter report, the patient preliminary encounter report containing predicted activity for a patient medical encounter, the patient preliminary encounter report adapted to receive annotations by a user, the predictor module producing an edited patient preliminary encounter report containing updated predicted activity in response to receiving the annotations; and
a rules engine having a processor for determining if the annotations to the patient preliminary encounter report meet a threshold level, the rules engine replacing the one or more stored rules with updated rules based on a result of determining if the annotations to the patient preliminary encounter report meet a threshold level,
the predictor module applying a subsequent set of patient characteristics to the updated rules to produce a subsequent patient encounter report, the subsequent patient encounter report including predicted activity for a subsequent patient medical encounter.

9. The system of claim 8, further comprising an event generating module for automatically generating at least one action upon submission of the annotations by the user.

10. The system of claim 9, wherein the at least one action includes one or more of generating a referral letter, issuing a medication prescription, generating financial transactions, ordering tests and sending information to a Health Information Exchange.

11. The system of claim 8, wherein the processor determines if the annotations to the patient preliminary encounter report meet a threshold level, at a physician level.

12. The system of claim 8, wherein the processor determines if the annotations to the patient preliminary encounter report meet a threshold level, at a healthcare facility level.

13. The system of claim 8, wherein the processor determines if the annotations to the patient preliminary encounter report meet a threshold level, at a patient level.

14. A computer program product tangibly embodied in a computer storage medium, for executing instructions on a processor, the computer program product being operable to cause a machine to:
apply patient characteristics to a stored set of rules to produce a preliminary patient encounter report, the preliminary patient encounter report including predicted activity for a patient medical encounter;
present the preliminary patient encounter report for editing
receive edits to the preliminary patient encounter report;
produce an edited patient encounter report containing updated predicted activity in response to the editing;
determine if the edits to the preliminary patient encounter report meet a threshold level;
replace the stored set of rules with updated rules based on a result of determining if the edits to the preliminary patient encounter report meet a threshold level; and
apply a subsequent set of patient characteristics to the updated rules to produce a subsequent patient encounter report, the subsequent patient encounter report including predicted activity for a subsequent patient medical encounter.

15. The computer program product of claim 14, wherein the computer program product automatically generates at least one action upon submission of the edited patient encounter report.

16. The computer program product of claim 15, wherein the at least one action includes one or more of generating a referral letter, issuing a medication prescription, generating financial transactions, ordering tests and sending information to a Health Information Exchange.

17. The computer program product of claim 14, wherein the computer program product determines if the edits to the preliminary patient encounter report meet a threshold level at a physician level.

18. The computer program product of claim 14, wherein the computer program product determines if the edits to the preliminary patient encounter report meet a threshold level at a healthcare facility level.

19. The computer program product of claim 14, wherein the computer program product determines if the edits to the preliminary patient encounter report meet a threshold level at a patient level.

20. The computer program product of claim 14, wherein the computer program product automatically determines if the edits to the preliminary patient encounter report meet a threshold level when the editing of the preliminary patient encounter report occurs.

* * * * *